United States Patent [19]

Psaros

[11] Patent Number: 5,501,212

[45] Date of Patent: Mar. 26, 1996

[54] IN-LINE DEHUMIDIFYING DEVICE EXPOSED TO THE AMBIENT ENVIRONMENT

[75] Inventor: Georgios Psaros, Tullinge, Sweden

[73] Assignee: Siemens Aktiengesellschaft, Munich, Germany

[21] Appl. No.: 311,900

[22] Filed: Sep. 26, 1994

Related U.S. Application Data

[63] Continuation of Ser. No. 944,266, Sep. 14, 1992, abandoned.

[30] Foreign Application Priority Data

Sep. 25, 1991 [SE] Sweden ................................. 9102777

[51] Int. Cl.$^6$ .............................. A62B 7/10; A62B 23/02; A62B 19/00; A61M 16/00
[52] U.S. Cl. ............................... 128/205.12; 128/204.18; 128/204.16; 95/52; 96/8
[58] Field of Search ........................ 128/201.13, 203.12, 128/204.13, 205.12, 207.14, 207.8, 911, 912, DIG. 26, 204.18, 204.15, 204.16; 95/52, 47; 96/8

[56] References Cited

U.S. PATENT DOCUMENTS

| | | | |
|---|---|---|---|
| 3,735,558 | 5/1973 | Skarstron et al. | 95/52 |
| 3,735,559 | 5/1973 | Salemme | 95/52 |
| 4,509,359 | 4/1985 | Gedeon et al. | 128/719 |
| 4,583,996 | 4/1986 | Sakata et al. | 95/52 |
| 4,783,201 | 11/1988 | Rice et al. | 95/52 |
| 4,909,810 | 3/1990 | Nakao et al. | 95/52 |
| 4,944,776 | 7/1990 | Keyser et al. | 95/52 |
| 4,947,339 | 8/1990 | Czekajewski et al. | 128/205.12 |
| 4,958,075 | 9/1990 | Mace et al. | 128/205.12 |
| 4,967,744 | 11/1990 | Chua | 128/912 |
| 4,985,055 | 1/1991 | Thorne et al. | 128/205.12 |
| 5,002,590 | 3/1991 | Friesen et al. | 95/52 |
| 5,013,331 | 5/1991 | Edwards et al. | 96/8 |
| 5,030,251 | 7/1991 | Rice et al. | 95/52 |
| 5,034,025 | 7/1991 | Overmann, III | 95/52 |
| 5,067,971 | 11/1991 | Bikson et al. | 95/52 |
| 5,071,448 | 12/1991 | Bikson et al. | 95/52 |
| 5,084,073 | 1/1992 | Prasad | 95/52 |
| 5,131,387 | 7/1992 | French et al. | 128/205.12 |
| 5,158,584 | 10/1992 | Tamura | 96/8 |
| 5,187,972 | 2/1993 | DeFriez | 128/205.12 |

FOREIGN PATENT DOCUMENTS

| | | | |
|---|---|---|---|
| 0048943 | 4/1982 | European Pat. Off. | 128/204.13 |
| 2222711 | 9/1990 | Japan | 95/52 |
| 9108826 | 6/1991 | WIPO | 95/52 |
| 9114476 | 10/1991 | WIPO | 128/205.12 |

OTHER PUBLICATIONS

*Hawley's Condensed Chemical Dictionary*, 11th ed, Sax & Lewis, Sr. eds, Van Nostrand, ©1987, ISBN 0-442-28097-1, p. 805.
"Perma Pure Dryers," Bulletin 104, Perma Pure Products, Inc., Farmingdale, N.J. 07727. no date.
"Gould Godart Fleish Flow Transducers," Bulletin PP101, Gould, Inc., Oxnard, CA 93030.
"Servo Ventilator 900 C," Operating Manual, Siemens-Elema AB, Solna, Sweden, 6th ed., Aug. 1988, pp. 10:2–10:6, pub. #AG088812.
"Star Exhalation Isolation System," Operating Instructions, Siemens Version, Infrasonics, San Diego, CA, 92121 Pub. #9910053, Apr. 1988.
"Expired Gas Cooling Device," Attwood et al, Methodist Hospital, IN., Oct. 6, 1989.

*Primary Examiner*—Kimberly L. Asher
*Attorney, Agent, or Firm*—Hill, Steadman & Simpson

[57] ABSTRACT

A dehumidifying device for use in a ventilator for reducing the relative humidity of the expired air of a patient has a plurality of tubes, permeable to moisture, arrayed in a bundle and encircled by a loosely wound spiral harness between a first connection section and a second connection section in the dehumidifying device. When gas expired by the patient reaches the dehumidifying device, the water vapor therein diffuses into the tubes, and the relative humidity of expired gas is decreased.

13 Claims, 2 Drawing Sheets

IN-LINE DEHUMIDIFYING DEVICE EXPOSED TO THE AMBIENT ENVIRONMENT

This is a continuation of application Ser. No. 07/944,266, filed Sept. 14, 1992, now abandoned.

BACKGROUND OF THE INVENTION

1. Field of the Invention

The present invention relates to a dehumidifying device intended for connection to an expiratory line of a ventilator before an expiratory flow meter.

2. Description of the Prior Art

The task of a ventilator, or a respirator, is to supply a patient with a breathing gas or anesthetic gas. This may occur in intensive care, in surgery when anesthesia is administered to the patient, to support spontaneous breathing or to impose a respiratory rate on a patient incapable of spontaneous respiration. The flow of expiratory gas is measured in the ventilator's expiratory section as a part of the ventilator's control function.

Sometimes a bacteria filter is also connected to the expiratory section to prevent the patient's bacteria and virus from escaping into ambient air. Since gas from the patient is expired gas, its temperature is relatively high, about 30° to 35° C., and the gas is saturated with moisture, i.e. its relative humidity is 100%.

This high humidity can cause major problems due to water condensation in the flow meter and bacteria filter. Condensation in the bacteria filter makes it more difficult for the patient to breathe, since condensate increases resistance in the expiratory section. One prior art flow meter is described in the Operating Manual for the Servo Ventilator 900 C, Siemens-Elema AB, publication no. AG 0888 12, Aug. 1988, pp. 10:2–10:6. This flow meter contains a mesh through which expired air flows from the patient. If the relative humidity of the patient's expired air is too high when passing the mesh, condensation could form on the mesh, thereby disrupting the flow meter function sufficiently to produce an erroneous measurement of air flow and thereby affect the operation of the entire ventilator.

Another type of flow meter is described in Bulletin PP101, Gould Godart Fleish Flow Transducers, Gould Inc. This flow meter has a system of channels through which the gas runs. Determination of the pressure on both sides of the channel system provides a measure of the flow from the pressure gradient. At a high relative humidity, water could condense in the channel and obstruct the channel with an ensuing increase in the pressure gradient across the channel system, leading to an erroneous value for flow.

When such a fault occurs, the flow meter must be removed from the ventilator, cleaned, dried, reinstalled and calibrated. Since calibration is particularly important and cannot be performed with a patient connected to the ventilator, one flow meter cannot merely be replaced with another. The entire ventilator must be replaced. This naturally creates needless, irritating extra work for staff. Therefore, avoiding this type of error is particularly desirable.

A drop of approximately 20% in humidity (moisture content) is sufficient to guarantee flow meter operation. Although such a goal may appear simple to achieve, many different methods and designs have been tried over the years in attempts to solve the problem. One such design is described in the aforementioned Operating Manual for the Servo Ventilator 900C, page 1:3, and is based on heating the flow meter to about 60'C in order to reduce the relative humidity. As is well-known, the ability of air to hold water varies directly with its temperature.

Another solution to the problem is described in the brochure Star Exhalation Isolation System, Operating Instructions, Siemens version, Infrasonic Inc., form no. 9910053, Apr. 1988. A device is connected to the ventilator's expiratory inlet to heat expired air passing through the device; the device is also equipped with a water trap to collect condensed water.

Yet another solution employs a cooling device for condensing water vapor in expired gas before the gas is fed into the ventilator's flow meter. The device is described in the article "Expired Gas Cooling Device" by J. Attwood and L. Bartel, of the U.S. However, the different methods and designs have the disadvantage of either being inadequate in reducing relative humidity sufficiently or being bulky, clumsy units which have to be connected to the ventilator or which are dependent on a reliable power supply. This means that greater reserve power capacity or batteries would be needed in the event of a power failure or when a portable ventilator is used. Additional equipment also increase the staff's work load when connecting the patient, and equipment must be monitored the entire time the patient is connected.

The equipment's bulky design is also a problem, especially when patients have to be transported while connected to the ventilator.

SUMMARY OF THE INVENTION

It is an object of the present invention to provide a simple, compact, efficient and energy-sparing dehumidifying device for use in a ventilator.

The above object is achieved in accordance with the principles of the present invention in a dehumidifying device, connectable in a ventilator as described above before the expiratory flow meter, the dehumidifying device having a plurality of tubes permeable to moisture, preferably made of fluorosulfonyl polymer, attached so as to constitute part of the expiratory line and so that expired gas passes through the tubes, in which the relative humidity of expired gas is reduced to a level at which the flow meter is not affected by the moisture, preferably less than 80%.

A number of materials permeable to moisture are known and have been used for drying gases. One known device (Bulletin 104, Perma Pure Products Inc.) includes a conduit containing a number of separate tubes made from hygroscopic material. The tubes are connected at each end of the conduit so a gas can traverse the conduit through the tubes. The conduit also has an opening at either end through which a desiccative gas can flow so water vapor is transferred to the desiccative gas. In this way, a completely dry gas can be obtained and fed to a moisture-sensitive equipment for analysis.

These materials have also been used in the ventilator/respirator field. Swedish Patent No. 428 345, corresponding to U.S. Pat. No. 4,509,359, describes a procedure for drying part of a patient's inspired or expired gas for measurement of the concentration of different component gases. A small part of the patient's inspired or expired gas volume is diverted through a tube made of fluorosulfonyl polymer or some other material with corresponding properties. The tube is completely exposed to ambient air. If a long enough tube is used, the temperature and moisture content of diverted gas will equilibrate to the temperature and relative humidity of ambient air. This is sufficient for obtaining satisfactory measurement results, since measurement instruments can be calibrated for ambient temperature and relative humidity.

However, the disadvantage of the latter device is that the room containing the patient must be air conditioned, when a ventilator/respirator has to be connected for a long period of time, as e.g. in intensive care, to ensure that measurement results are reliable. In addition, this system cannot be regarded as appropriate when patients on a ventilator/respirator must be transported, since ambient temperature and relative humidity can then vary considerably.

Despite the fact that these materials have been known for a long time, even in the ventilator/respirator field, and despite the fact that the problem of condensation in the flow meter has been known even longer, no solution according to the present invention has ever been presented or proposed.

To the contrary, professionals in the field, as shown by the above, have made major efforts to make external devices for heating expired gas or designed different kinds of water traps to collect condensed water after expired gas was cooled.

Even from the technical point of view, significant insight and creativity are needed to achieve this solution to a problem which has existed for such a long time in the field.

Because each individual tube has an internal diameter which is less than the internal diameter of the expiratory line, a more effective contact surface between gas and ambient air is obtained. Drying then takes place more rapidly, and tubes can be shorter without any impairment of results.

An advantageous refinement of the dehumidifying device is obtained according to the invention by arraying the tubes in a bundle between the respective tube-to-expiratory line attachment areas.

This makes it easier to design a compact dehumidifying device while providing the tubes with greater protection than when they are completely separated. Even though the tubes are arrayed in a bundle in which only the outermost tubes are directly exposed to ambient air, experiments have shown that even the innermost tubes in the bundle make a major contribution to the drying of ambient air.

To further reduce the risk of damage to tubes by external force, it would be an advantage to surround the tubes with protection which still permits ambient air to reach the tubes.

Protection in the form of a loosely applied spiral harness which encircles the tubes between the respective tube-to-expiratory line attachment areas can be used. The tubes would then be well-protected while still leaving the peripheral tubes exposed to ambient air. A mesh wound around the tubes, or rings threaded onto the tubes, are other conceivable forms of protection.

In order to attain strong, leak-resistant and problem-free tube-to-expiratory line attachment areas, each attachment area can include a disc with holes, a locking element with holes and a gasket with holes between the disc and the locking element, the tubes passing through the holes, the locking element fixed in a position compressing the gasket, the gasket then expanding in a radial direction and pressing against the metal sockets of the tubes.

The compressed gasket keeps the tubes in a fixed position. Radial gasket expansion also creates a contact seal around each tube, thereby minimizing the risk of gas leakage.

Each tube may have a socket, preferably made of non-rusting metal, at the gasket. The socket can prevent tube deformation when the gasket is pressed against the tubes.

Since the internal diameter of the metal sockets is the same as the internal diameter of the tubes, there is no narrowing which could affect gas flow.

If the gasket is designed so the diameter of a cross section through each hole decreases toward the middle of the gasket, the gasket's contact with each tube will be more efficient and the force more evenly distributed, since the rounding provides a little additional space for the gasket's radial expansion.

To prevent the dehumidifying device from constituting a stricture in the ventilator system, the device has been designed so the total cross-sectional area of the tubes is at least as large as the smallest cross-sectional area of the rest of the expiratory section.

A further refinement of the dehumidifying device according to the invention is obtained by having the dehumidifying device removably attached to the expiratory line, the respective attachment area consisting of a first connector section and a second connector section. This makes the dehumidifying device compact and easy to replace, thereby facilitating device cleaning.

In this context, preferably all the components in the dehumidifying device are made of materials capable of withstanding autoclaving.

DESCRIPTION OF THE PREFERRED EMBODIMENTS.

Figure 1:
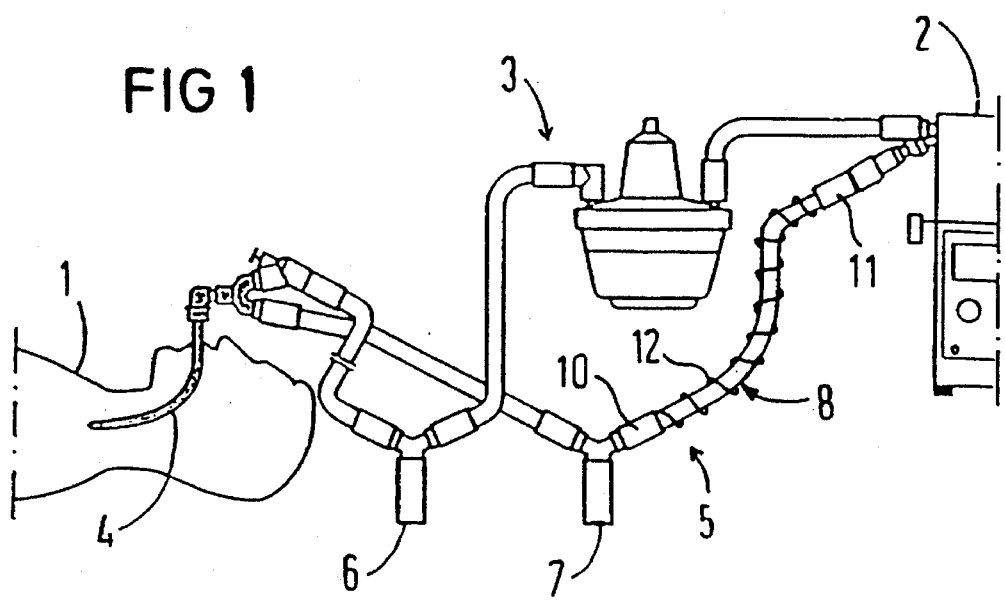
FIG. 1 shows a ventilator with a dehumidifying device, constructed in accordance with the principles of the present invention, connected to a patient.

A patient 1 requiring a special mixture of breathing gas, or requiring mechanically assisted artificial ventilation, is usually connected to a ventilator 2 only shown in part in FIG. 1. Breathing gas is fed from the ventilator 2 to the patient 1 through an inspiratory line 3 and then to the lungs through a breathing tube 4.

An expiratory line 5 conducts expired gas from the patient 1 to the ventilator 2. The flow of, e.g. expired gas is measured in the ventilator 2.

The inspiratory line 3 has a first water trap 6 for collecting any condensed water forming in the inspiratory line 3. A second water trap 7 located in the expiratory line 5 has the same function. The risk of water condensation is much greater in the expiratory line 5, since expired gas is saturated, i.e., it has a relative humidity of 100%, and is relatively warm, about 33° C. When expired gas is cooled in the expiratory line 5 by the lower ambient temperature, water condenses and runs down into the second water trap 7. However, the relative humidity of expired gas remains unchanged, and if this expired gas is allowed to pass the flow meter in the ventilator 2, the risk of disruption to flow meter operation is very considerable.

In order to substantially eliminate this risk, part of the expiratory line 5 consists of a dehumidifying device 8 which reduces the relative humidity of expired gas to a level harmless to the flow meter, i.e. a maximum relative humidity of about 75–80%.

Figure 2:
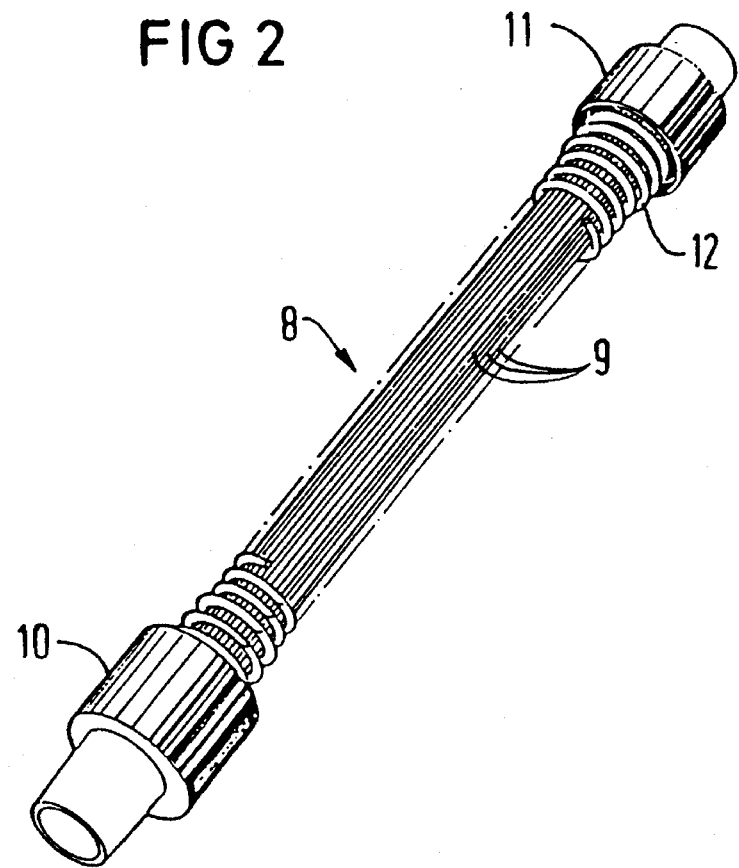
FIG. 2 shows the dehumidifying device in more detail.
Figure 3:
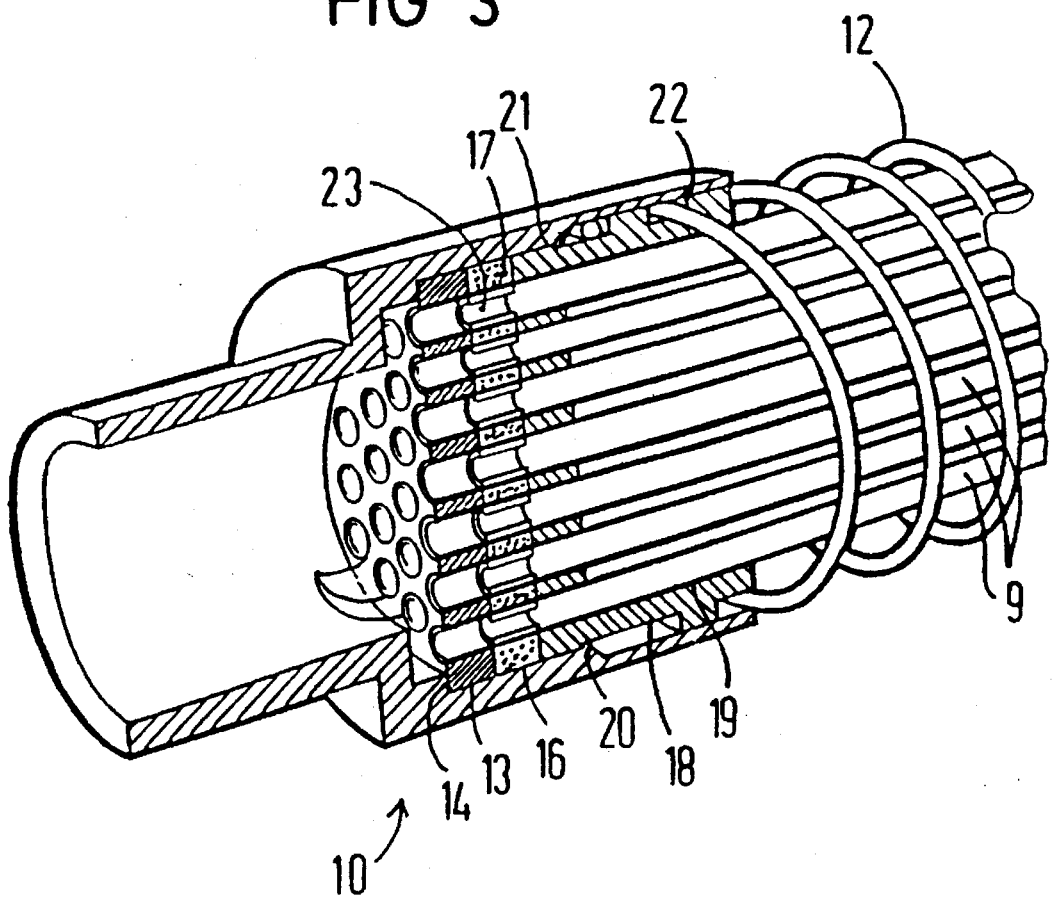
FIG. 3 shows an enlarged part of the dehumidifying device in cross-section.

FIGS. 2 and 3 show how the dehumidifying device 8 is designed with a plurality (for example, 37) of tubes 9 made of a material permeable to moisture (i.e., having a moisture-permeable tube wall) such as fluorosulfonyl polymer. The tubes 9 are attached between a first connector section 10 and a second connector section 11. The tubes 9 are about 300 mm long, but the length can be varied, depending on how large or small a reduction in the relative humidity of expired gas is desired. A 300 mm length is sufficient for expired gas to attain the same temperature and relative humidity as ambient air.

The tubes 9 are arrayed in a bundle encircled by a loosely wrapped spiral harness 12 between the first connector section 10 and the second connector section 11.

The harness 12 has only been shown at the respective connector sections 10 and 11 in FIG. 2 to illustrate how the tubes 9 are bundled. The spiral harness 12 protects the tubes 9 from external force, however, it is still sufficiently loose to permit ambient air to come into contact with the peripheral tubes 9.

As shown in FIG. 3, the connector section 10 has a disk 13 against a boss 14 in the first connector section 10. The disk 13 has holes 15 through which the tubes 9 can pass. A gasket 16 also equipped with holes 17 for the tubes 9, is adjacent to the disk 13, and a locking element 18 also equipped with holes 19, is disposed next to the gasket 16.

After the tubes 9 are inserted into in the holes 15, 17 and 19, the locking element 18 is pressed against the disk 13 and then is fixed in this position by pressing a region 21 of increased diameter of the locking element 18 against a projection 20 on the inside of the first connector section 10, is and then snapped in place.

Since the locking element 18 has a spiral track 22 the spiral harness 12 can be fixed in position at the first connector section 10 without any additional fittings.

The second connector section 11 is devised in an identical manner.

Compression of the gasket 16 causes it to expand radially, leading to a reduction in the size of the holes 17 in the gasket 16, and the gasket 16 is pressed against the outer sides of the tubes 9, thereby fixing them radially in position while simultaneously sealing the 10 first connector section 10 at the entry point for the tubes 9.

To prevent deformation of the tubes 9 by pressure from the gasket 18, a non-rusting metal socket 23 can be incorporated as a part of each tube 9 at the gasket 16 position. The metal socket 23 supports the tube 9 of which is a part and improves sealing. Since the internal diameter of the metal socket 23 is identical to the inner diameter of the tube 9, there are no problems with constrictions impeding air flow.

Figure 4:
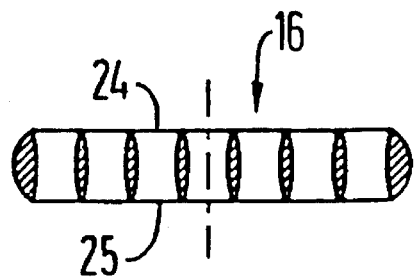
FIG. 4 shows a cross section of a gasket in the dehumidifying device.

As shown in FIG. 4, which shows the gasket 16 in an uncompressed state, the holes 17 in the gasket 16 are rounded in a cross section through the gasket 16 so the diameter of the holes 17 decreases from each of the upper and lower sides respectively 24 and 25 of the gasket towards the middle of the gasket 16. This design facilitates compression of the gasket and at the same time makes the force against the tubes 9 more uniform and more controlled than if the holes 17 had a straight cross section.

Although modifications and changes may be suggested by those skilled in the art, it is the intention of the inventor to embody within the patent warranted hereon all changes and modifications as reasonably and properly come within the scope of his contribution to the art.

I claim as my invention:

1. A ventilator comprising:
   an expiratory line and an expiratory flow meter, said expiratory line disposed before said expiratory flow meter, and said expiratory line carrying moisture-containing expired gases having a relative humidity from a patient;
   and a dehumidifying device consisting of a plurality of tubes including an outer layer of tubes, means for permitting connection of said tubes in said expiratory line where said tube form a continuous in-line section of said expiratory line and the entirety of expired gases flow through said tubes, and with at least a portion, including said outer layer, of said plurality of tubes exposed directly and openly to ambient atmosphere without an airflow-impeding barrier;
   and each of said tubes having a moisture-permeable tube wall for exchanging moisture between the expired gases therein and ambient atmosphere, said tubes forming, in combination, means for reducing the relative humidity of said expired gases to a relative humidity of less than 80%.

2. A dehumidifying device as claimed in claim 1 wherein said tube walls consist of fluorosulfonyl polymer.

3. A dehumidifying device as claimed in claim 1 wherein said expiratory line has an internal diameter, and wherein each of said tubes has an internal diameter which is less than said internal diameter of said expiratory line.

4. A dehumidifying device as claimed in claim 3 wherein said tubes are arrayed in a bundle between said means for permitting connecting of said tubes in said expiratory line.

5. A dehumidifying device as claimed in claim 1 further comprising means surrounding said tubes for protecting said tubes while permitting ambient air to reach said tubes.

6. A dehumidifying device as claimed in claim 5 wherein said means for protecting comprises a spiral harness loosely encircling said tubes between said means for permitting connecting of said tubes in said expiratory line.

7. A dehumidifying device as claimed in claim 1 wherein said means for permitting connection of said tubes in said expiratory line includes two attachment areas, spaced from each other with said tubes therebetween, with each attachment area including a disc having holes therein for respectively receiving said tubes, a locking element having holes therein in registry with said holes in said disc, and a gasket having holes therein in registry with said holes in said disc and said locking element, said gasket being disposed between said disc and said locking element with said tubes passing through said holes in each of said locking element, said gasket and said disc, and means for fixing said locking element in a position for compressing said gasket.

8. A dehumidifying device as claimed in claim 7 wherein each tube has a socket consisting of non-rusting metal surrounding each tube within a respective hole in said gasket.

9. A dehumidifying device as claimed in claim 8 wherein each socket has an internal diameter equal to the internal diameter of each tube.

10. A dehumidifying device as claimed in claim 7 wherein each hole in said gasket has a cross section with a diameter which decreases toward a middle of said gasket.

11. A dehumidifying device as claimed in claim 1 wherein said ventilator has an expiratory section, including said expiratory line, said expiratory section having a portion thereof with a smallest cross-sectional area for transmitting expiratory gas, and wherein said tubes have a total cross-sectional area at least equal to said smallest cross-sectional area.

12. A dehumidifying device as claimed in claim 1 wherein said means for permitting connection of said tubes in said expiratory line comprises means for removably attaching said tubes to said expiratory line, and includes a first connector section and a second connector section.

13. A dehumidifying device as claimed in claim 12 wherein said dehumidifying device consists entirely of materials capable of withstanding autoclaving.

* * * * *